United States Patent [19]

Tennant

[11] 4,261,065

[45] Apr. 14, 1981

[54] ARTIFICIAL INTRAOCULAR LENS WITH FORWARD-POSITIONED OPTICS

[76] Inventor: Jerald L. Tennant, 122 W. Colorado, Dallas, Tex. 75208

[21] Appl. No.: 61,267

[22] Filed: Jul. 27, 1979

Related U.S. Application Data

[63] Continuation of Ser. No. 716,423, Aug. 23, 1976, abandoned.

[51] Int. Cl.³ .......................... A61F 1/16; A61F 1/24
[52] U.S. Cl. ......................................................... 3/13
[58] Field of Search ........................................ 3/13, 1

[56] References Cited

U.S. PATENT DOCUMENTS

| | | | |
|---|---|---|---|
| 2,834,023 | 5/1958 | Lieb | 3/1 |
| 3,673,616 | 7/1972 | Fedorov et al. | 3/13 |
| 3,711,870 | 1/1973 | Deitrick | 3/13 |
| 3,906,551 | 9/1975 | Otter | 3/13 |
| 3,913,148 | 10/1975 | Potthast | 3/13 |
| 3,922,728 | 12/1975 | Krasnov | 3/13 |
| 3,925,825 | 12/1975 | Richards et al. | 3/13 |
| 3,971,073 | 7/1976 | Richards et al. | 3/13 |
| 3,991,426 | 11/1976 | Flom et al. | 3/13 |

FOREIGN PATENT DOCUMENTS

| | | | |
|---|---|---|---|
| 959314 | 3/1957 | Fed. Rep. of Germany | 3/13 |
| 1034325 | 7/1958 | Fed. Rep. of Germany | 3/13 |
| 1103399 | 5/1955 | France | 3/13 |

OTHER PUBLICATIONS

"The Mark VI, Mark VII and Mark VIII Choyce Anterior Chamber Implants" by Peter Choyce, *Proceedings of The Royal Society of Medicine*, vol. 58, Sep. 1965, pp. 729-731.

*Primary Examiner*—Ronald L. Frinks

[57] ABSTRACT

An artificial intraocular lens adapted to fixate in the sclera of the eye while positioned in the anterior chamber with supporting structure to prevent contact between the posterior surface of the lens and the iris, thus preventing postoperative glaucoma.

8 Claims, 6 Drawing Figures

ARTIFICIAL INTRAOCULAR LENS WITH FORWARD-POSITIONED OPTICS

This is a continuation of application Ser. No. 716,423 filed Aug. 23, 1976 now abandoned.

BACKGROUND OF THE INVENTION

1. Field of the Invention

The present invention relates to opthalmology and more particularly to artificial lenses used to restore binocular vision in aphakia.

2. Discussion of the Prior Art

Properly constructed artificial intraocular lenses are known to produce stable retinal images when placed in the eye. A major problem of intraocular lens implantation is the fixation of the lens in, in front of, or behind the pupillary aperture. In the prior art Flom U.S. Pat. No. 3,866,249 uses lenses with prongs, Potthast U.S. Pat. No. 3,913,148, and Richards and Grolman U.S. Pat. No. 3,925,825, use clips, Fedorov U.S. Pat. No. 3,673,616 and Binkhorst, Deitrick U.S. Pat. No. 3,711,870 uses suturing and Otter U.S. Pat. No. 3,906,551 and Krasnov U.S. Pat No. 3,922,728 employ combinations of the above. These devices have been unsatisfactory from a variety of standpoints, mostly related to difficulty with fixation in the eye without causing damage to the ocular structures.

The fibrous sclera of the eye is the most suitable structure of the eye from which to support a plastic lens implant. The only place where the sclera presents itself inside the eye where it is accessible for fixation is the "scleral spur", an annular ring of sclera near the area where the iris and cornea meet. This area is called "the angle" (of the anterior chamber). Fixation to the scleral spur produces pure and stable scleral fixation.

Most of the lenses noted above are fixed to the iris or to remnants of the lens capsule left behind when a cataract is removed. The iris is a flimsy, vascular, mobile structure. Fixation of the plastic lens implant to the iris or lens capsule by means of sutures, loops, clips, scar tissue, etc., leaves a lens which is still mobile and capable of damaging the adjacent, delicate ocular structures.

Dr. Peter Choyce of London provided a lens in which a support system is contoured to fit in the angle against the scleral spur without appendages or suturing. Dr. Choyce's lenses eliminate some of the aforementioned problems. However, the Choyce lens introduces inherent problems caused by the various positioning mechanisms. Its biconcave, posteriorly placed optic does not allow for clearance of the iris beneath the lens. This contact of the iris with the lens blocks the normal flow of fluid in the eye, resulting in increased intraocular pressure (acute glaucoma). This requires more surgery to alleviate the glaucoma. West German Pat. No. 959,314 discloses a lens similar in some respects to the Choyce lens.

Accordingly, the present invention, is an improvement over the Choyce lens and obviates the need for prongs, loops, clips, incisions, and sutures, and most importantly moves the optical lens structure anteriorly in the eye with the object of prevention of glaucoma caused by contact of the lens posterior with the iris.

The optical lens structure is anteriorly convex with the posterior surface being either planar or convex. Binkhorst, 6 Ophthalmic Surgery 17 (1975) teaches that an optical lens structure, wherein the posterior surface is planar, is superior to other configurations. Thus, a planar posterior surface is the preferred embodiment.

SUMMARY OF THE INVENTION

The aforesaid objective is accomplished by supporting the lens posterior off of the transiridial plane by means of two supporting members integral with the lens and with two feet which rest in the angle on the scleral spur. Each foot has a toe cardioid in shape which holds the lens in situ.

DRAWINGS

A more complete understanding of the invention may be had by referring to the following detailed description when taken in conjunction with the drawings, wherein.

DETAILED DESCRIPTION

Figure 3:
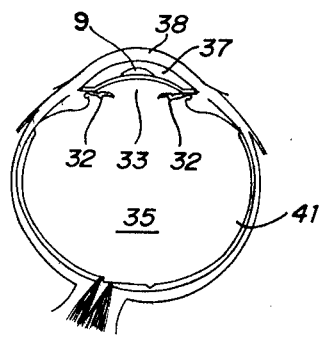
FIG. 3 is a cross-sectional view of the eye showing the lens in situ.

FIGS. 1-5 illustrate an artificial lens adapted to fixate in the scleral spur of the eye while positioned in the anterior chamber. The structure comprises an optical lens section 9 and supporting structure 6.

The lens 9 is formed of a material which is biologically inert, i.e., not suspectible to being absorbed by the body fluids and capable of being well tolerated by the human body when implanted. An exemplary material is polymethyl methacrylate. The anterior surface 10 of lens 9 is convex. The posterior surface 11 is planar. A planar surface is preferred because of its superior optical properties. The thickness of the lens 9 along the optical axis 14 (FIG. 5) is variable depending upon the power of the lens.

The artificial lens structure comprising an optical lens portion 9 and supporting structure 6 is preferably manufactured as an integral unit and is homogeneous in composition. The supporting structure 6 comprises solid arches 8 terminating in feet 7. Arches 8 are integral with the lens 9 and with feet 7.

Arches 8 all have the form of a medial slice out of an inverted disk with a flat bottom; the parallel vertical sides 19 are tangent to the circumference of the lens 9.

Each foot 7 has two toes 21 forming a cardoid like edge 20 shaped to hold the supporting structure 6 in situ in the anterior chamber of the eye. The sides of foot 7 are parallel to the longitudinal axis of the structure and along the outside of each toe 21 are rectilinear.

Figure 6:
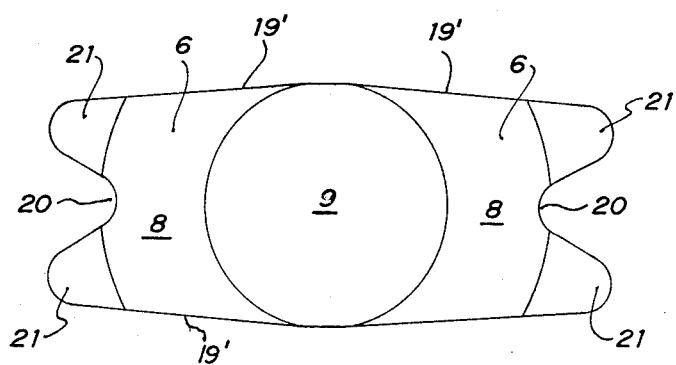
FIG. 6 is a top view of a modification of the invention.

The lens in FIG. 6 is much the same as the lens of FIGS. 1-5 except that the sides of the invention 19' tangent to lens 9 are nonparallel, angled in the inward direction of feet 7.

It will be apparent that the above described supporting structure is not limited to a structure consisting of supporting members and feet. The foot structure supports the lens anteriorly off the iridial plane thereby to avoid or reduce glaucoma.

Figure 2:
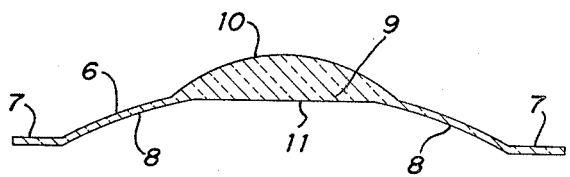
FIG. 2 is a cross-sectional view taken along line 2—2 of FIG. 1.
Figure 4:
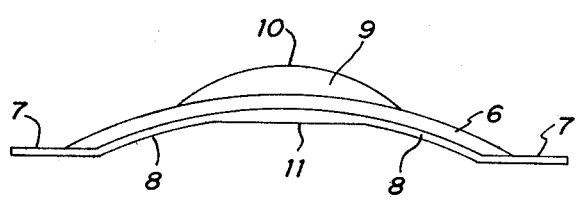
FIG. 4 is a side elevational view of the lens of FIGS. 1-3.
Figure 5:
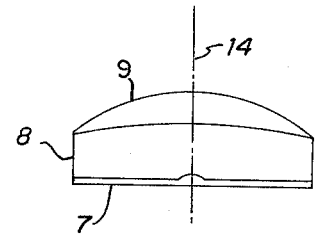
FIG. 5 is an end view of the lens of FIGS. 1-4.
Figure 1:
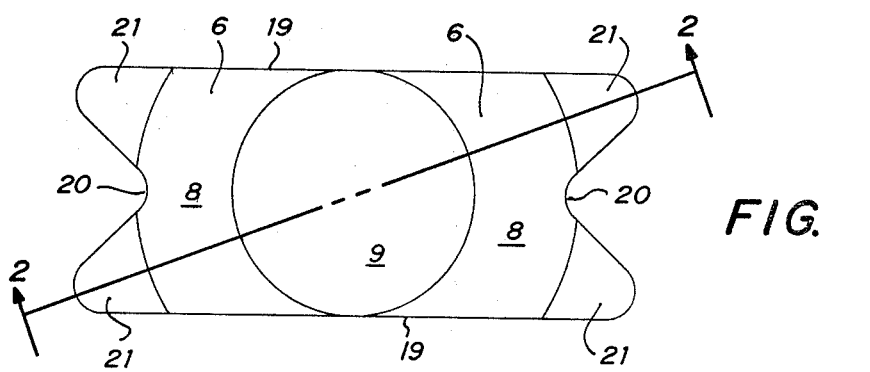
FIG. 1 is a top view of a lens embodying the present invention.

In FIG. 2 the optical lens 9 shape in its preferred embodiment is shown wherein the anterior surface 10 is convex and the posterior surface 11 is planar and supported by arches 8 from feet 7 as to be clear of the iris, thereby avoiding problems attendant to the irritation resulting from operative procedures during removal of the natural lens and the implant thereof.

Exemplary dimensional parameters of the particular embodiment of the invention described in FIGS. 1 through 5 are:

diameter of lens 9=6.0 mm.
lateral dimension of foot 7=6.0 mm.
thickness of lens 9 along the optical axis 14, variable according to the power of the lens.
thickness of foot 7 perpendicular to the ciliary area=0.25 mm.
distance from toe to toe=11.0 −14.0 mm in 0.5 mm steps.

The distance from the transiridial plane to the lens posterior along the optical axis 14 preferably is about $\frac{3}{4}$ mm.

In FIG. 3, the lens 9 is illustrated as inserted into an eye 41. Posterior chamber 35 is separated from anterior chamber 37 by the iris 32. The iris 32 is comprised of spongy tissue has a central aperture or pupil 33. The cornea 38 defines the outside boundary of the anterior chamber 37. During surgical implantation of the intraocular lens, an incision is made in the cornea 38, and the cornea 38 is carefully lifted away to permit surgical entry into the eye 41. After the natural lens is removed, the lens structure is then positioned in the anterior chamber of the eye anterior to the iris 32.

The intraocular lens 9 functions by supporting the optical structure anterior to the iris and holding the lens stationary in front of the pupillary aperture by means of the supporting structure which extends to the boundary of the anterior chamber, thereby minimizing irritation to the iris and glaucoma.

Although particular embodiments of the invention have been illustrated in the drawings and described herein, it will be understood that the invention is not limited to the embodiments disclosed, but is capable of rearrangement, modification and substitution of parts and elements without departing from the spirit of the invention.

What is claimed is:

1. An artificial lens adapted to be fixed into the sclera of the eye while positioned in the anterior chamber which comprises:

(a) an arched unitary structural support adapted to lie entirely within said chamber having coplanar oppositely directed supporting feet which are of a length and dimension to extend to the boundary of said chamber and which are shaped to fix the position thereof within said chamber, and (b) an optical lens formed in said structural support anteriorly convex and posteriorly shaped for spacing the posterior surface of said lens about 0.75 millimeters above the plane of said feet for substantial clearance above the plane of said feet adapted to be positioned with the posterior surface of said lens substantially anterior to the iris of the eye to avoid contact therewith.

2. The combination set forth in claim 1 in which said support structure and said lens are both unitary and homogeneous in composition with said support structure including an arch terminating in said feet, the toes of which are spaced apart forming cardioid shaped ends to hold the structure in situ in the anterior chamber of the eye.

3. The combination set forth in claim 1 in which said two feet extending in diametrically opposed directions away from said lens are interconnected by said arch in which said lens is formed, said arch having the form of a medial slice out of an inverted disc with a bottom shaped to be maintained in spaced relation anteriorly of the iris of the eye to avoid contact therewith.

4. An artificial lens as defined in claim 3 wherein the supporting members are solid arches interiorly dished spaced above the plane of said feet having parallel vertical sides tangent to the circumference of the lens.

5. An artificial lens as defined in claim 1 wherein said supporting structure comprises arches interiorly dished having convergent sides tangent to the circumference of the lens.

6. An artificial lens as defined in claim 1 wherein the edges of each said foot are rectilinear.

7. An artificial lens as defined in claim 1 wherein the posterior of said lens is planar.

8. An artificial lens adapted to be fixed into the sclera of the eye while positioned in the anterior chamber which comprises:

an optical lens structure anteriorly convex and posteriorly planar;
two diametrically opposed coplanar feet extending away from said lens; and
two supporting members forming an arch and each unitary with said lens and rooted in said feet outside the perimeter of said lens and supporting said lens with the posterior thereof being positioned substantially anterior to the plane of said feet by spacing the posterior surface of said lens about 0.75 millimeters from the plane of said feet for avoiding contact between said posterior surface and the iris of the eye.

* * * * *